United States Patent [19]

Moore

[11] Plant 4,596

[45] Sep. 30, 1980

[54] MINIATURE ROSE PLANT

[76] Inventor: Ralph S. Moore, 2519 E. Noble Ave., Visalia, Calif. 93277

[21] Appl. No.: 44,413

[22] Filed: Jun. 1, 1979

[51] Int. Cl.[3] ..... A01H 5/00

[52] U.S. Cl. ..... Plt./4

[58] Field of Search ..... Plt./3–4

*Primary Examiner*—Robert E. Bagwill

[57] ABSTRACT

The subject of the present disclosure is a new and distinct variety of miniature rose plant characterized by the orange-yellow color of buds and flowers and further identified by semi-climbing or trailing habit of plant growth making it desirable for container or hanging basket culture.

1 Drawing Figure

1

The present invention relates to a new and distinct variety of hardy, semi-climbing (trailing) rose plant of the miniature class; the variety being primarily characterized — as to novelty — by medium orange-yellow buds and flowers which in general color effect are similar to Sundust, miniature (not patented).

The variety is further characterized by:

An abundance of bloom, with flowers borne singly or several together in loose clusters on terminal shoots and on shorter lateral shoots along the main stems.

Light sweet fragrance.

A plant which is vigorous, of semi-climbing or trailing habit, with small matt foliage and pointed leaflets; the buds and flowers being similar in form and size to Magic Wand (climbing miniature — not patented) with the present variety having more petals.

The plant, which has a normal height of 10–12 inches may spread out horizontally to 30 inches or more.

A plant which grows and blooms satisfactorily especially outdoors; is good for growing in pots; planters, hanging baskets and as a ground cover.

The present variety of miniature rose was originated by me at Sequoia Nursery located at Visalia, Calif., under conditions of careful control and observation, as a cross between seedling #1-72-1 (a climbing yellow miniature — used only for breeding) as the seed parent and Magic Wand (miniature climber — not patented) as the pollen parent.

Subsequent to origination of the variety I successfully asexually reproduced it at Sequoia Nursery, located as aforesaid, by budding as well as by cuttings; the reproductions having run true in all respects.

The color photograph illustrates the variety, including the foliage, buds and flowers.

Referring now specifically to the new and distinct variety of miniature rose plant, the following is a detailed description thereof in outline; all major color plate identifications being by reference to the British Colour Council Horticultural Colour Chart, except where common terms of color definition are employed.

Type: Hardy; semi-climber (trailing); bushy; rounded; seedling; outdoors; cut flowers; garden decoration; potted plant.

Class: Miniature.

*Variety name.*—Orange Cascade.

Flowers borne: Singly and several together (3 to 5) on tips and on lateral shoots.

Quantity of bloom: Abundant especially outside.

2

Bud:

*Peduncle.*—Medium to short length; slender; erect; medium to light green often tinted reddish; hairs — numerous fuzz-like hairs.

*Before calyx breaks.*—Size — small. Form long: pointed with numerous soft hairs and several foliaceous appendages on surface of bud; with foliaceous parts extending beyond the tip of the bud equal to about one-half of its length. Color — medium green with sepals often tinted bronze.

*As calyx breaks.*—Color — orange-yellow — near Cadmium Orange 8/2.

*Opening.*—Opens well in all weather.

Bloom:

*Size when fully open.*—Small, averaging about 30 mm (1¼").

*Petalage.*—Double — averaging about 45 petals, arranged regularly plus sometimes several small petaloids.

*Form.*—Cupped at first, becoming rounded, with petals rolled loosely outward, and later at maturity more open with stamens showing.

Petals: Fairly thin; satiny on inside and on outside surface.

*Shape.*—Outside petals, broad lanceolate with rounded tip; intermediate — broad lanceolate, rounded with small acute tip; inside — lanceolate with acute or rounded tip.

Color: Newly opened flower from a plant grown outdoors.

*Outside petal.*—Outside surface — near Cadmium Orange 8/2 becoming more yellow toward base. Inside surface — near Tangerine Orange 9/2 becoming more yellow at base. (Orange color may be deeper in cooler weather — sometimes overlaid with a deeper reddish tint).

*Intermediate petal.*—Outside surface — similar to outside petal. Inside surface — similar to outside petal.

*Inner petal.*—Outside surface — same as intermediate petal; inside surface — same as intermediate petal. General color effect; newly opened flowers — color medium orange-yellow. Three days open — color similar to newly opened flowers but lighter color (more yellow). Behavior — opens well in all weather. Color deeper in cool weather. Spent petals drop off. Flower longevity (May 1979) — plant in pot 4–5 days. Cut flowers at living room temperature 3–4 days.

Reproductive organs:

*Stamens.*—Moderately abundant, arranged regularly about pistils.

*Filaments.*—Quite short, yellow.

*Anthers.*—Well formed; yellow.

*Pollen.*—Very small amount.

*Pistils.*—Moderate number.

*Styles.*—Fairly even; very short; bunched; color — dark; reddish.

*Stigmas.*—Off white or yellowish.

*Ovaries.*—All enclosed in calyx.

*Hips.*—None.

*Sepals.*—Permanent; spear shaped; recurved.

*Seed.*—None.

Foliage:

*Leaves.*—Compound of five or seven leaflets (usually seven); quite small; leathery; matt.

*Leaflets.*—Shape: broad lanceolate; nearly oval; apex acute; base rounded or rounded acute. Margin serrate. Color: medium green; new growth — normal (medium ) green. Rachis: medium strength; upper side may have numerous tiny short hairs and several small foliaceous thorn-like growths; grooved; underside moderately thorny, with several short hairs and tiny prickles. Stipules: medium long; narrow to medium width; short length narrow points which turn out usually at less than 45 degrees. These points are often curved inward toward rachis.

Growth:

*Habit.*—Semi-climbing or trailing; bushy; much branched.

*Growth.*—Free vigorous; internodes short.

*Canes.*—Medium; slender; sturdy.

*Main stems.*—Color: medium green.

*Thorns.*—Average; slender; hooked (curved) slightly downward; color; dark reddish or brown. Prickles — few or none; hairs — none.

*Branches.*—Color: light to medium green. Thorns: average; medium length; slender; curved, inclined slightly downward. Medium to short oval base. Prickles: none. Hairs: none.

*Young shoots.*—Color: light to medium green. Thorns: average, slender; curved, inclined slightly downward; color — reddish.

The miniature rose plant and its flowers as herein described may vary in slight detail due to climatic, soil and cultural conditions under which the variety may be grown; the present description being of the variety as grown at Visalia, Calif.

The following is claimed:

1. A new and distinct variety of miniature rose plant of hardy, much branched, semi-climbing, or trailing habit, substantially as illustrated and described, characterized by buds and flowers of a medium orange-yellow color, the buds and flowers resembling Magic Wand in size and shape with the present variety having more petals; and further characterized by a plant of vigorous compact growth habit with abundant, almost fern-like foliage, said plant being easy to propagate from soft wood cuttings or by budding, with an abundance of flowers born usually in small clusters on shoot tips and on short lateral stems arising along the longer main stems.

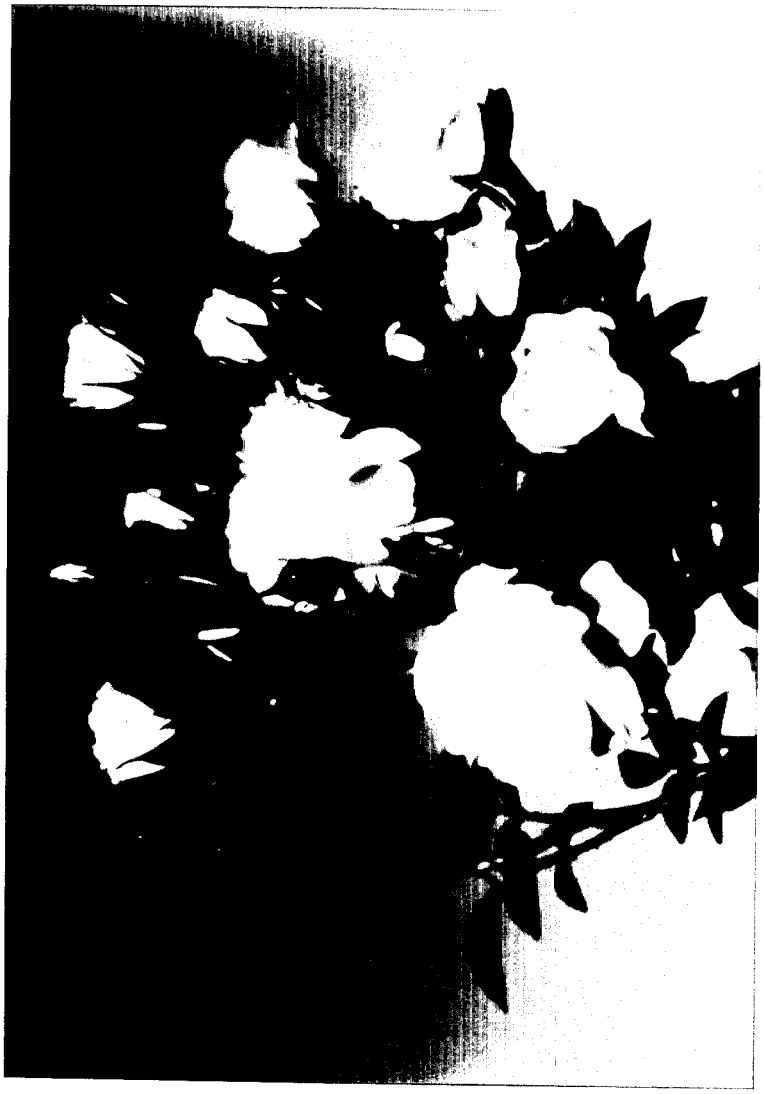

* * * * *